United States Patent
Briscoe et al.

(10) Patent No.: US 12,352,735 B2
(45) Date of Patent: Jul. 8, 2025

(54) APPARATUS AND METHODS FOR PREDICTING GAS SENSOR SENSITIVITY CHANGES

(71) Applicant: BLACKLINE SAFETY CORP., Calgary (CA)

(72) Inventors: Michael Briscoe, Calgary (CA); Lohrasp Seify, Calgary (CA); Justin Miller, Calgary (CA)

(73) Assignee: BLACKLINE SAFETY CORP., Calgary (CA)

( * ) Notice: Subject to any disclaimer, the term of this patent is extended or adjusted under 35 U.S.C. 154(b) by 239 days.

(21) Appl. No.: 18/022,045

(22) PCT Filed: Aug. 17, 2021

(86) PCT No.: PCT/CA2021/051132
§ 371 (c)(1),
(2) Date: Feb. 17, 2023

(87) PCT Pub. No.: WO2022/036441
PCT Pub. Date: Feb. 24, 2022

(65) Prior Publication Data
US 2023/0349874 A1 Nov. 2, 2023

Related U.S. Application Data

(60) Provisional application No. 63/067,093, filed on Aug. 18, 2020.

(51) Int. Cl.
*G01N 33/00* (2006.01)

(52) U.S. Cl.
CPC ................. *G01N 33/0006* (2013.01)

(58) Field of Classification Search
CPC .............. G01N 33/0006; G01N 33/007
See application file for complete search history.

(56) References Cited

U.S. PATENT DOCUMENTS

| | | |
|---|---|---|
| 6,741,919 B1 | 5/2004 | Schuster et al. |
| 7,143,630 B2 | 12/2006 | Studer et al. |
| 7,584,069 B2 | 9/2009 | Guichard et al. |
| 8,543,340 B2 | 9/2013 | Tice |
| 10,139,291 B2 | 11/2018 | Todd et al. |
| 10,251,588 B2 | 4/2019 | Liang et al. |

(Continued)

FOREIGN PATENT DOCUMENTS

| | | | |
|---|---|---|---|
| GB | 2516893 A | * 2/2015 | ........... G01N 33/007 |
| GB | 2580634 A | 7/2020 | |

(Continued)

*Primary Examiner* — Eric S. McCall
*Assistant Examiner* — Anthony W Megna Fuentes
(74) *Attorney, Agent, or Firm* — Dilworth IP, LLC (57) ABSTRACT

Methods and apparatus for monitoring gas sensor sensitivity. The method includes repeatedly determining the response of a gas sensor by exposing the gas sensor to a gas and measuring the gas sensor response; and transmitting the response, information identifying the gas detector, and the time of the calibration to a remote computer. The remote computer then calculates a trend of sensitivity for the gas detector over time based on the received responses and corresponding time values and determines a renewal time when the calculated trend intersects a predetermined value.

20 Claims, 6 Drawing Sheets

(56) References Cited

U.S. PATENT DOCUMENTS

| | | |
|---|---|---|
| 10,346,228 B2 | 7/2019 | Ramanath et al. |
| 10,610,141 B2 | 4/2020 | Böhm et al. |
| 2004/0055359 A1 | 3/2004 | Ketler et al. |
| 2017/0208493 A1 | 7/2017 | Masson et al. |
| 2018/0035931 A1 | 2/2018 | Hoss et al. |
| 2019/0261904 A1 | 8/2019 | Ma et al. |
| 2019/0294998 A1 | 9/2019 | Kloepper et al. |
| 2020/0096476 A1 | 3/2020 | Yan et al. |
| 2020/0169945 A1 | 5/2020 | Crouthamel et al. |

FOREIGN PATENT DOCUMENTS

| | | | |
|---|---|---|---|
| JP | 05080027 A | 3/1993 | |
| JP | 6182052 B2 | 8/2017 | |
| WO | 2015019067 A1 | 2/2015 | |
| WO | WO-2019152047 A1 * | 8/2019 | ......... G01N 33/0067 |

* cited by examiner

APPARATUS AND METHODS FOR PREDICTING GAS SENSOR SENSITIVITY CHANGES

FIELD OF THE INVENTION

The invention relates to gas detectors, associated methods and systems. In particular, the invention relates to monitoring and/or predicting the sensitivity of gas sensors.

BACKGROUND

Gas monitoring devices or gas detectors include devices which are configured to monitor a user or an environment in order to determine whether there is a danger.

In situations where there is a risk of hazardous gas, the area around the risk is monitored by gas measurement devices. In the industry, these devices are commonly referred to as "area monitors". These area monitors house gas sensors. The sensors detect the concentration levels of various gases. When the gas levels for a particular gas reach a predetermined threshold, the area monitor will signal with an alarm. The alarm typically consists of lights, sound and often remote transmission of the alert.

Generally, the sensors also require periodic calibration due to normal changes in sensitivity that sensors exhibit over their service life. A calibration is performed by exposing the monitor to a known concentration of gas for a defined length of time to adjust the sensor readings for accuracy.

A bump test is a shorter functional test of a gas monitor. Sensors and alarm indicators are tested, ensuring acceptable performance of sensors and monitor before use. All sensors are challenged with a known quantity of gas, and instrument response is measured to ensure that it will function to an acceptable level.

JP 2013/232,876 discloses a method of predicting sensor use life using sensitivity values of a gas sensor which are acquired by calibration processing performed on the gas sensor with a standard gas.

U.S. Pat. No. 7,143,630 B2 discloses a gas-measuring device has an electrochemical sensor and features such that the readiness for use is guaranteed for a determined period of time based on a current integral of the sensor current. A status display is activated by the evaluating circuit of the gas-measuring device. The status display displays the degree of depletion of the sensor.

SUMMARY

In accordance with the invention, there is provided a method for monitoring gas sensor sensitivity comprising:
  repeatedly determining the response of a gas sensor by exposing the gas sensor to a gas and measuring the gas sensor response; and
  transmitting the response, information identifying the gas detector, and the time of the calibration to a remote computer; and
  using the remote computer to:
    calculate a trend of sensitivity for the gas detector over time based on the received responses and corresponding time values;
    determine a renewal time when the calculated trend intersects a predetermined value; and
    report the renewal time.

The renewal time may be considered to correspond to when the gas sensor sensitivity needs to be replaced because it is no longer sufficiently sensitive to properly detect the gas. The reported renewal time may allow a replacement sensor to be provided or obtained to replace the existing sensor.

The response may be a parameter (e.g. resistivity, voltage change) of the gas sensor measured over the time that the gas sensor is exposed to the gas. The remote computer may be configured to determine a sensitivity value from the raw response. In other embodiments, the response may be a determined sensitivity value determined by the gas detector from a parameter of the gas sensor which changes when it is exposed to the gas.

A sensitivity value may correspond to the steady state or stable response of a gas sensor to a constant concentration of gas.

A sensitivity value may be determined by a bump test, wherein the sensitivity value is determined based on the dynamic response of the gas sensor to the gas. For example, the dynamic response may be used to determine what the steady state or stable response would be if the sensor was exposed to a constant concentration of gas for an extended period of time. The dynamic response may correspond to a rising portion of the response (i.e. where the response is changing towards a value corresponding to the presence of gas). All the sensitivity values used to calculate the renewal time may be determined by bump tests.

A bump test may have a duration of less than 45 seconds. The duration of the bump test may correspond to the time between test gas being introduced into the environment of the sensor and the sensor providing a response which meets one or more bump-test criteria (e.g. the response exceeds a predetermined value).

A bump test may be configured to end before the gas sensor response has stabilized. A bump test may be configured to end before or after an inflection point is detected in the sensor response (e.g. to a constant concentration of gas). The bump test may end by stopping exposing the gas sensor to the test gas and/or stopping recording the response of the gas sensor to the test gas.

A sensitivity value may be determined during a calibration, wherein the sensitivity value is determined based on the stable response of the gas sensor to the gas. This means that a calibration typically takes longer than a bump test because it requires that the response of the sensor is stable before it is complete. A calibration may have a duration of more than 60 seconds. A calibration may have a duration of more than 120 seconds. A calibration may have a duration of less than 600 seconds. All the sensitivity values used to calculate the renewal time may be determined by calibrations. The duration of the calibration may correspond to the time between test gas being introduced into the environment of the sensor and the sensor providing a response which meets one or more calibration criteria (e.g. the response being stable for a predetermined period of time).

The gas detector may be configured to measure the flow rate of gas past the gas sensor. This may be used to normalize the response based on the quantity of gas which is passing the gas sensor.

The method may comprise:
  determining a bump-test sensitivity value by a bump test;
  determining a calibration sensitivity value by a calibration; and
  adjusting, based on the calibration, at least one of: the bump-test sensitivity value and a confidence interval associated with the bump-test sensitivity value.

The method may comprise:
  determining a bump-test sensitivity value by a bump test;

determining a calibration sensitivity value by a calibration;

assigning confidence intervals to the bump-test and calibration sensitivities, wherein the bump-test confidence interval is larger than the calibration confidence interval.

The method may comprise using the remote computer to detect anomalous results by identifying determined sensitivity values which are outside the calculated sensitivity trend.

The method may comprise using the remote computer to calculate a fit coefficient, the fit coefficient being a measure of the variance of the sensitivity data over time with respect to the calculated trend; and to adjust the determined renewal time based on the calculated fit coefficient.

The renewal time may be re-calculated after each determination of a sensitivity value.

The gas detector may be configured to measure environmental conditions at the time of the calibration, and transmit the measured environmental conditions to the remote computer; and wherein the remote computer is configured to calculate the trend of sensitivity based on the most recent determined sensitivities which are within a predetermined environmental condition range.

The environmental conditions may comprise one or more of: humidity, pressure and temperature.

The gas detector may be configured to measure the location of the gas detector at the time of the calibration, and transmit the measured location to the remote computer; and wherein the remote computer is configured to calculate the trend of sensitivity based on the most recent determined sensitivities which are within a predetermined location range.

The remote computer may be configured to determine the mathematical form of the trend based on sensitivity data received from other gas sensors of the same type.

The mathematical form of the trend may be one or more of: linear decline and exponential decay.

The remote computer may be configured to identify a gas sensor replacement by detecting a jump in sensitivity followed by a decline in sensitivity following a new trend.

The trend may be monitored over at least 3 months. The trend may comprise at least 10 received sensitivity values from the gas detector.

The gas sensor may have a unique identification code (e.g. number) which is transmitted with the sensitivity values. This allows the sensitivity values to be associated with a particular gas sensor. The gas detector may have a unique identification code which is transmitted with the sensitivity values.

To compare tests, it will be appreciated that tests may be compared directly when performed under the same conditions. For example, the response of the sensor in one sensitivity determination (e.g. from the dynamic response of a bump test) may be compared with the response of during a second sensitivity determination (e.g. the stable response of a calibration) if the sensor is set up the same way for both tests (e.g. the configuration of the sensor, the concentration of gas etc.). In some cases, to compare the responses, the response values must be scaled or normalized. For example, the response may be scaled if a different concentration or flow rate of gas is used for different tests. Likewise, if the voltage applied across the sensor is changed from sensitivity test to another, this may have to be accounted for. To the extent that the effect of these changes is well known, they can be taken into account to allow one sensitivity determination to be compared with another sensitivity determination. These adjustments may affect the units of the graph. For example, where conditions and configurations are kelp constant, the sensitivity values may be reported as a raw response value. In cases where the conditions or configurations have changed, the sensitivity values may be reported in normalized or scaled values (e.g. raw response per concentration of gas).

Reporting the renewal time may comprise displaying the renewal time on a display. Reporting the renewal time may comprise transmitting the renewal time to a further computer.

Sensitivity value determinations may be performed manually (i.e. with a user interacting with the gas detector to perform the test). Sensitivity value determinations may be performed autonomously by the gas detector with no user present (e.g. using on-board test gas sources). Sensitivity value determinations may be performed in response to a predetermined schedule. Sensitivity value determinations may be performed in response to a request (e.g. transmitted from a remote computer).

The gas sensor may be housed in a chamber with an opening configured to allow gas interaction with the environment. The opening may be covered with a mesh. The gas sensor may be replaceable.

The chamber may be connected to the environment via a channel (e.g. a tube). The channel may comprise a flow meter. The gas detector may be configured to switch to a test mode in response to detecting flow through the channel. The chamber may comprise a one-way valve to prevent gas entering the chamber via the channel.

The gas detector may be configured to determine the initiation of a sensitivity value determination in response to detecting a response in the gas sensor (e.g. when in a test mode).

According to a further aspect, there is provided a system for monitoring gas sensor sensitivity comprising:

repeatedly determining the response of a gas sensor by exposing the gas sensor to a gas and measuring the gas sensor response; and transmitting the response, information identifying the gas detector, and the time of the calibration to a remote computer; and the remote computer configured to:

calculate a trend of sensitivity for the gas detector over time based on the received sensitivity values and corresponding time values;

determine a renewal time when the calculated trend intersects a predetermined value; and report the renewal time.

According to a further aspect, there is provided a method for determining gas sensor sensitivity comprising:

performing a bump test by exposing a gas sensor to a gas and measuring the dynamic gas sensor response;

comparing the dynamic response to one or more calibration curves;

determining a sensitivity value.

The gas detector and/or the remote computer may be configured to calculate a sensitivity value based on the response of a gas sensor to the gas.

The gas detector may be configured to enable (e.g. initiate) two-way communication with the remote computer in response to a user interaction or an alarm being activated.

The gas detector may comprise mounting points for the one or more gas sources, the mounting points being configured to rigidly hold the gas sources (e.g. gas cylinders) in place. Therefore, if the transportable gas detector is moved, the gas sources can be more easily moved with the gas detector.

A gas source may be considered to be a container for gases. A gas source may be a gas cylinder or tank. A gas source may be a pressure vessel for storage and containment of gases at above atmospheric pressure. High-pressure gas cylinders are also called bottles. Inside a gas source the stored contents may be in a state of compressed gas, vapor over liquid, supercritical fluid, or dissolved in a substrate material. A typical gas cylinder design is elongated, standing upright on a flattened bottom end, with the valve and fitting at the top for connecting to the gas inlet.

The transceiver may be configured to use wired or wireless communication. The transceiver may be configured to use one or more of: cellular radio Satellite communication, wide-area network (WAN), infrared, BlueTooth™ and Wi-Fi.

The gas monitor may be configured to communicate with a remote computer. The remote computer may be a remote server. The server may be monitored by a plurality of computing devices connectable to the remote server. This allows one alert on the server to be seen by multiple potential helpers via the computing devices. The remote server may be configured to store data received from the gas monitor in alert mode (e.g. including the two-way (e.g. voice or text) communication, threat data, location of user and/or time of threat being detected).

The gas monitor may be configured to enable multiple modes of voice communication.

The gas monitor may be configured to transmit information to the remote computer in response to the battery level going below a predetermined threshold (e.g. when the battery is about to run out) and/or in response to the amount of gas in the gas sources going below a predetermined threshold (e.g. when there is insufficient gas in a source to perform a test). The gas monitor may be configured to transmit battery and/or gas source information to the remote computer (e.g. periodically or upon request). The gas monitor may be configured to display battery and/or gas source information.

The remote computer may be a central server, cloud or other device. The remote computer (e.g. cloud) may make the information available at a variety of terminals (e.g. smartphone or computer via a log-in) via the internet.

The gas monitor may comprise a location detector. The location detector may comprise: a GPS module. The location detector may be configured to use local fixed-point anchor-node signaling to determine location (e.g. fixed Wi-Fi points). The location detector may use cellular networks to determine location. The location detector may comprise an indoor positioning system (IPS).

The one or more threat sensor may be configured to sense one or more of the following environmental parameters: concentration of a particular gas; airflow; temperature of the environment; humidity; radiant heat; sound intensity and light intensity.

A monitoring gas monitor may include one or more of: a gas sensor, processing circuitry, one or more motion or accelerometer sensors, one or more gyroscope or shock sensors, one or more two-way communication modules, one or more physiological sensors, one or more mode sensors, transmitter circuitry and receiver circuitry.

The gas monitor, remote computer or system may comprise processing circuitry to calculate, assess and/or determine values based on the sensor data. The processing circuitry may include memory (for example, Flash memory, DRAM and/or SRAM) to store, and transmitter circuitry to send and receive information over the cellular, satellite or other such communication network, said sensor data and information which is representative of environmental conditions (for example, atmospheric carbon dioxide). The gas monitor, machine(s), processor(s) (suitably programmed) and/or field programmable gateways (or combinations of the aforementioned)) may be employed to calculate, determine, assess and/or determine one or more values based on sensor data.

Sensors and networking circuits may include, for example, one or more accelerometers, gyroscopes, compasses, global positioning system receiver, short range wireless circuits which may include ANT or Bluetooth™ or other short-range protocols, multicast wireless sensor, to calculate and/or detect the location of the user and transmit sensor data. Some gas monitors are configured to use, for example, 3G and satellite wireless connections. This mitigates the need for Wi-Fi networks, infrastructure and/or Bluetooth™ connections.

The gas detector may be configured to initiate and perform its own baseline (zeroing), bump test and/or calibration. This may reduce or eliminate the need for manually initiated bump tests or calibrations as well as reducing or eliminating the need for interfacing with a docking station. This will allow the gas monitor to be remotely tested and maintained in the field for extended lengths of time without human intervention.

The gas detector may comprise or be connectable to containers for gas (e.g. $CO_2$, $NH_4$). Gas from these containers can be introduced into a chamber containing the sensor to test whether the sensor is still working. When not being tested, the gas detector is configured to monitor gas from the environment which enters the chamber through a gas-permeable section (e.g. a mesh portion).

A gas detector may be one of the following types:
Portable: designed to carried by the user
Transportable, moveable but designed to be set in place for an extended period of time (days to months); and
Fixed: designed to be permanently in place.

A fixed gas detector may be an area monitor. The gas detector may be able to perform bump tests and calibrations for itself (e.g. using an on-board or connected supply of test gas). This may reduce the need for an operator to travel though potentially dangerous areas of the facility. That is, automatic testing may reduce the risk for employees.

The gas detector may be configured to enable the processes of generating alerts based on pre-determined levels or sensor thresholds.

The gas detector may be configured to enable the processes of two-way communication based on transmission or triggering of pre-determined levels or sensor thresholds.

The gas detector may be configured to use interchangeable sensors. The gas monitor or system may be configured to use integrated sensors.

The gas detector may comprise a user interface. The user interface may include one or more output mechanisms (for example, a display and/or speaker) and/or one or more input mechanisms (for example, a microphone, and sensor and tactile gesture recognition sensor(s)); notably, any manner of and/or mechanism for outputting and/or inputting of data and/or commands (for example, responses to, for example, queries) are intended to fall within the scope of the present disclosure.

The gas detector may comprise a single unit. The gas monitor may comprise multiple units in communication with each other. For example, the gas monitor system may comprise a gas detector unit in communication (e.g. wireless communication such as Bluetooth™) with a portable electronic device with a controller and a transmitter (e.g. a mobile phone or laptop).

A gas detector may comprise a controller comprising a processor and a memory having computer program code. A remote computer may comprise a controller comprising a processor and a memory having computer program code.

Also encompassed within the present disclosure are corresponding methods for using the gas detectors and systems described above.

Also encompassed within the present disclosure are computer programs for configuring the gas detectors and systems described above to perform their functions. Such computer programs may be stored on non-transitory media such as CDs.

BRIEF DESCRIPTION OF THE DRAWINGS

Various objects, features and advantages of the invention will be apparent from the following description of particular embodiments of the invention, as illustrated in the accompanying drawings. The drawings are not necessarily to scale, emphasis instead being placed upon illustrating the principles of various embodiments of the invention. Similar reference numerals indicate similar components.

FIG. 1b is a schematic view of the gas detector of FIG. 1a.

FIG. 1d is a cross-section view of a portion of the gas detector of FIG. 1a.

DETAILED DESCRIPTION

Introduction

Industrial chemicals leaked, spilled, or mishandled are common risks within environments such as manufacturing facilities. These facilities may have incorporated real-time gas detectors. Such an industrial facility may provide monitoring capability of remote situations, in multiple locations, and across multiple platforms or geographies. The gas detectors may include portable personal gas detectors that workers might use when in potentially dangerous environments (e.g. working in an industrial setting where there may be gas leaks).

All gas detectors should generally be regularly tested for functional capability to determine if they respond to targeted gases. This is called a bump test. A bump test is a brief exposure of the gas sensor to gas primarily in order to verify that the sensors respond and that the instrument alarms function accordingly.

The gas detectors typically also require periodic calibration due to normal changes in sensitivity that sensors exhibit over their service life. A calibration is generally performed by exposing the monitor to a known concentration of gas for a defined length of time to adjust the sensor readings for accuracy.

Bump testing is typically performed on the sensors once a day. Calibration is generally done once every 30 to 180 days depending on the system.

The present technology relates to monitoring the sensitivity of a gas sensor over time in order to predict when the sensitivity falls below a certain level. An aspect is fitting a trend line to a series of gas sensor sensitivity data points and predicting when the trend will hit a threshold sensitivity.

The system may be configured to perform one or more of the following:

Use Machine Learning to identify anomalous results.

Detect replacement of a sensor by detecting a step change in sensitivity followed by a further decline in sensitivity.

Select which data points to use based on location and/or environmental conditions (humidity, temperature, pressure).

Select which data points to use based on algorithmic outlier detection.

Determine the type of trend line to use based on other sensors of the same type.

In the course of the detailed description to follow, reference will be made to the attached drawings. These drawings show different aspects of the monitoring systems and, where appropriate, reference numerals illustrating like structures, components, materials and/or elements in different figures are labeled similarly. It is understood that various combinations of the structures, components, and/or elements, other than those specifically shown, are contemplated and are within the scope of the present inventions.

Moreover, there are many aspects and embodiments of the technology described and illustrated herein. The present disclosure is neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, certain permutations and combinations are not discussed and/or illustrated separately herein.

Various aspects of the invention will now be described with reference to the figures. For the purposes of illustration, components depicted in the figures are not necessarily drawn to scale. Instead, emphasis is placed on highlighting the various contributions of the components to the functionality of various aspects of the invention. A number of possible alternative features are introduced during the course of this description. It is to be understood that, according to the knowledge and judgment of persons skilled in the art, such alternative features may be substituted in various combinations to arrive at different embodiments of the present invention.

Portable Gas Detector

Figure 1A:
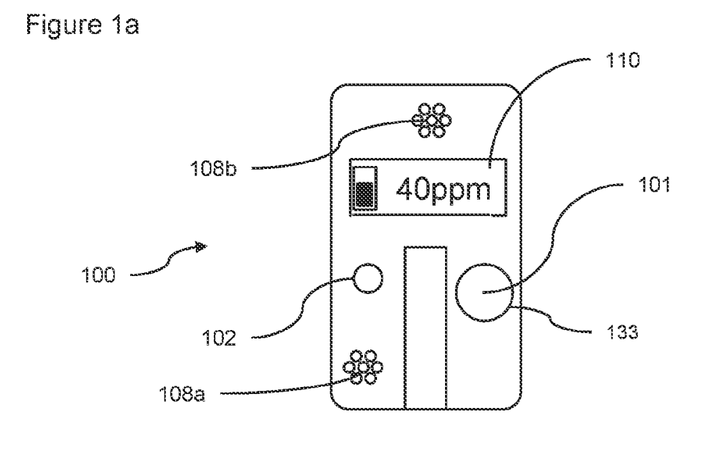
FIG. 1a is a front view of a gas detector.

FIG. 1a shows a portable personal gas detector 100. In this case, the portable personal gas detector comprises a gas sensor 101 (which is, in this embodiment, positioned in a chamber behind a mesh 133) configured to measure gas levels in the environment of the gas detector. In this case, the threat sensor comprises a carbon monoxide sensor. The level of threat is displayed on a display screen 110 of the gas detector 100.

The portable gas detector may also include, in addition to one or more gas sensors (e.g. of polymeric-type), a singular or plurality of accelerometers, gyroscopes, temperature sensors, humidity sensors, and pressure sensors.

It will be appreciated that other threat sensors may be configured to sense one or more of the following environmental parameters: concentration of a particular gas (e.g. toxic gases such as carbon monoxide, hydrogen sulfide, nitrogen dioxide); airflow; lower explosive limit (LEL); the temperature of the environment; the humidity; radiant heat; and light intensity.

The portable personal gas detector may comprise other threat sensors configured to sense, for example, one or more of the following user parameters: motion of the user (e.g. to detect whether the user has stopped moving or is moving in an way indicative of a problem); orientation of the user (e.g. to detect if the user has fallen); heart-rate of the user; time since user last initiated a report signal; and temperature of the user.

In this case, the sensor 101 of the portable personal gas detector is connected to a controller 104 (shown in FIG. 1b) comprising a processor 107 and a memory 105 having computer program code 106. The controller 104 is configured to activate an alarm 102 (in this case comprising a flashing light and an audio warning) if the gas levels, environmental or user parameters measured by the sensor 101 go beyond a predetermined range (e.g. corresponding to a dangerous level). In this case, the alarm 102 is configured to be activated in response to the carbon monoxide level being greater than 100 ppm (other values may be used such as 70 ppm). Both upper and lower alarm levels may be set.

Figure 1B:
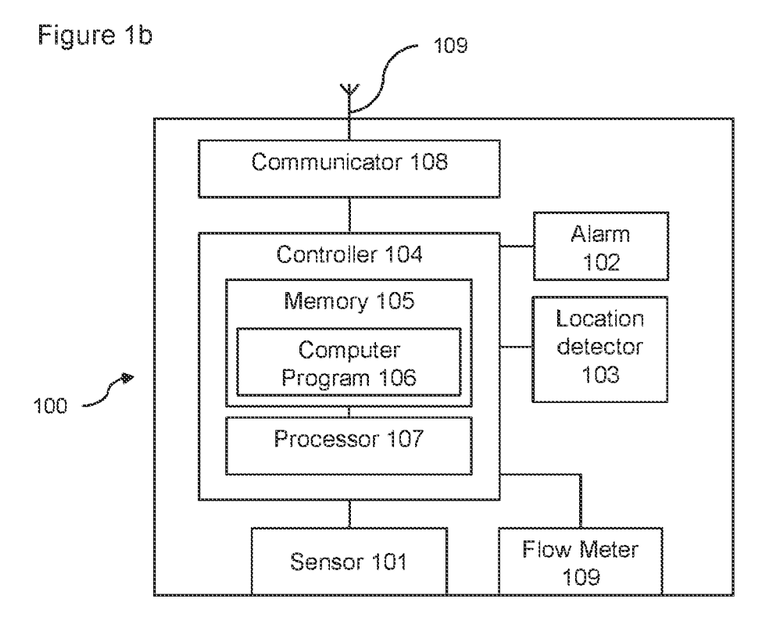

In this case, the personal gas detector also includes a communicator 108 comprising a microphone 108a and a speaker 108b configured to support two-way voice communication via a transceiver antenna 109 with a remote computer (e.g. a remote server or another personal gas detector of a 'buddy' nearby).

The personal gas detector is configured to communicate using a self-contained cellular communication module which may help reduce or eliminate much of the required infrastructure to provide remote notification type of alarm monitoring. Cellular communication also provides the wearer of the portable personal gas detector the ability to articulate their situation to an emergency response team. Furthermore, self-monitoring of the gas detectors may enable a remote site to know whether it is operating properly.

Such a compact and light weight safety monitoring system, capable of detecting atmospheric gas and/or other measures of sensor inputs, could be easily carried or worn by personnel in the area of interest, being the gas detector would be capable of operating without a fixed install. Transmitting data in real-time may allow the gas detector to remain connected regardless of the environment or location where it is being used. It may also allow data from multiple portable personal gas detectors to be collated and processed in real-time which may be important in developing situations.

The communication transceiver 109 is configured to freely and continuously send and receive voice and data over the air. In this case, the transceiver 109 is a cellular transceiver configured to connect to a cellular or mobile network (e.g. T-Mobile, AT&T, Verizon, etc.). This may help allow communications to be established while operating without local infrastructure constrains, such as Wi-Fi, telephone or internet cables. Other embodiments may use satellite infrastructure (i.e. Globalstar, Iridium, etc.), and geospatial technologies, (i.e. global positioning systems) or Wi-Fi, telephone or internet systems. In this case, the portable personal gas detector also comprises a location detector 103 configured to determine the location of the portable personal gas detector 100. In this case, the location detector 103 of the portable personal gas detector 100 is configured to determine its location using a combination of a satellite-based positioning systems, and beacons positioned within the environment.

In addition to deactivating the ability to receive a call, the portable gas detector is configured to transmit data to one or more remote computers. In this case, the alert is transmitted via non-voice.

Testing Mode

Figure 1C:
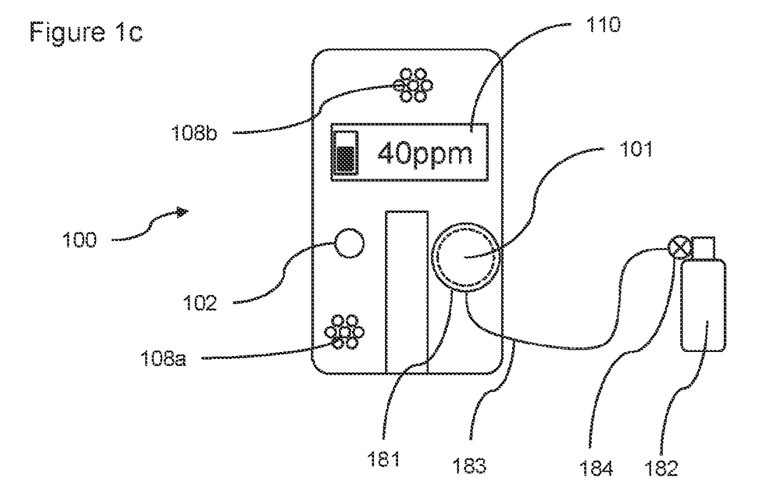
FIG. 1c is a front view of the gas detector of FIG. 1a while it is undergoing testing to determine a sensitivity value.
Figure 1D:
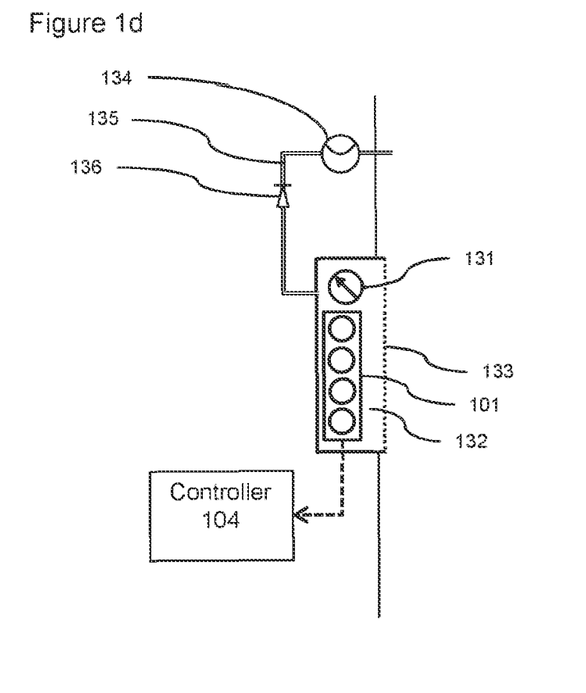

FIG. 1c shoes the gas detector undergoing a bump test. A similar configuration may be used for calibration. In the testing mode, in this case, the gas monitor is configured to deactivate the alarm to prevent the alarm being activated when test gas is introduced into the chamber. FIG. 1d is a cross-section view of a portion of the gas detector.

Other embodiments may be configured to activate the alarm during test mode to confirm to those in the vicinity that the gas monitor is working. Other embodiments may comprise a microphone configured to determine whether the audio alarm is sounding when activated by the controller. For example, when the alarm is activated by the controller, the controller may be configured to determine whether a sound corresponding to the alarm (e.g. having the correct volume and frequency) is detected by the microphone. If the audio alarm is not detected by the microphone, the controller may alert the remote computer via the transceiver.

In this embodiment, the testing mode is initiated by introducing a test gas into a chamber 132 in which the gas sensor 101 is located. In this case the chamber 132 also houses a pressure sensor 131. In this case, the chamber 132 housing the gas sensor has a mesh area to facilitate gas exchange between the chamber and the environment in normal use. The chamber also is connected to the exterior by a release channel 135. During a bump test, a cap 181 is placed over the mesh area 133 and gas is injected into the chamber via the cap through the mesh. The cap may be sealed over the mesh using a seal (e.g. a resilient O-ring seal). Gas is transmitted to the cap 181 from a vessel 182 via a valve 184 and a tube 183. Gas within the chamber is displaced through a channel 136 within the gas detector to the exterior.

In this case, the channel comprises a flow meter 134 to determine the rate at which gas is being injected into the chamber. The channel may also comprise a one-way valve 136 to prevent gas entering the chamber through this channel in normal use. Detecting the flow rate during the sensitivity tests allows a more accurate measure of the quantity of gas which is passing by the sensor. The flow meter may also allow the device to detect when a bump test is being performed. For example, the gas detector may be configured to switch to a test mode in response to detecting a flow through the channel in response to gas being injected into the chamber. This may allow the gas detector to automatically record the dynamic response of the gas sensor to the injected gas.

Figure 2:
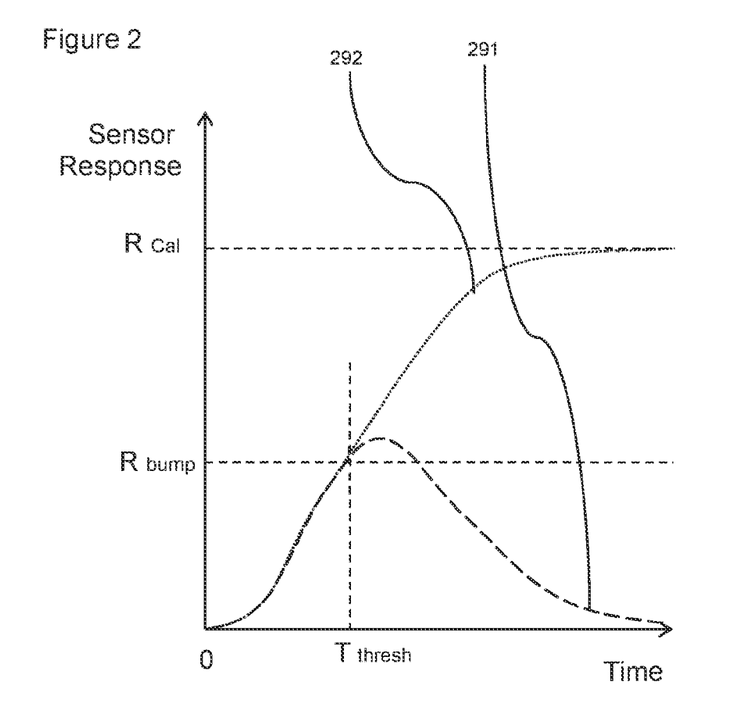
FIG. 2 is a graph of the sensor response with respect to period of time of gas exposure for a bump test and for a calibration.

For a bump test, the gas detector is configured to monitor the response of the corresponding gas sensor (e.g. the CO sensor when CO is introduced into the chamber). A bump test curve 291 is shown in FIG. 2. For the purposes of determining whether the gas detector is currently operable, in this case, the gas monitor is configured to determine whether the response of the gas sensor is greater than a predetermined bump threshold. This is shown in FIG. 2. At t=0, CO gas is introduced into the chamber and the CO sensor starts to respond. At t=$t_{thresh}$ the sensor response has reached the predetermined CO bump threshold, $R_{bump}$. It will be appreciated that the declining response of the sensor after the test has completed may or may not be recorded.

In this embodiment of FIG. 1c, the gas source is configured to introduce gas into the chamber for a predetermined period of time regardless of whether or not the sensor has reached the bump threshold, $R_{bump}$. Other gas detector embodiments may be configured to continue to introduce gas into the chamber for a predetermined period of time or until the sensor has reached the bump threshold, $R_{bump}$.

If the sensor does not reach the bump threshold response in the predetermined period of time, the sensor is considered not to have met the requirements of the bump test. The gas monitor may be configured to provide an audio and/or visual indication that the gas monitor is no longer monitoring that gas.

In other embodiments, if the sensor does not reach the bump threshold response in the predetermined period of time, the gas monitor is configured to run a calibration test (see below) and then to re-bump test the sensor. If the sensor does not reach the bump threshold response in the predetermined period of time after calibration, the sensor is considered not to have met the requirements of the bump test.

For a calibration, the gas monitor is configured to monitor the response of the corresponding gas sensor (e.g. the CO sensor when CO is introduced into the chamber). The calibration test curve 292 is shown in FIG. 2. In this case, the gas monitor is configured to determine the steady-state response of the sensor and then adjust the gas monitor accordingly.

In this case, the gas monitor is configured to continue to introduce test gas into the chamber for a predetermined period of time or until the sensor has reached a consistent response, $R_{Cal}$. The response may be considered consistent if the response is not varying within a predetermined range (e.g. ±5%) over a predetermined period of time (e.g. 5 seconds).

The inventors have realized that, in addition to determining if the gas detector is currently operable, information from a bump test may be used to calculate a sensitivity value based on the dynamic response of the gas sensor to the gas. That is, the dynamic response of the gas sensor over time during a bump test may be extrapolated (e.g. using previous calibrations) to determine a measure of the stable sensitivity value of the gas sensor. For example, a more rapid response (e.g. lower $T_{thresh}$) may be associated with a higher determined consistent response value, $R_{cal,\ inf}$. This may allow sensitivity values deduced from bump tests to be directly compared with sensitivity values deduced from calibrations, and/or sensitivity trends to be determined from bump tests. That is, the bump test data may be used to calculate indirectly the stable sensitivity value of the gas sensor.

Because, the ultimate sensitivity of the gas sensor is not measured directly, the error or uncertainty around the bump-test sensitivity value may be larger than the error or uncertainty around a calibration sensitivity value. However, because bump tests are typically performed much more frequently than calibration values, this error in individual sensitivity values can be counteracted by having a much larger number of readings (e.g. daily rather than monthly).

In this case, the gas monitor is configured to adjust itself based on the consistent response value, $R_{Cal}$. For example, the gas monitor may be configured to scale the sensor response in detection mode based on the consistent response value to calculate the level of gas present. For example, if the calibration determines that the gas sensor was less responsive (and had a lower consistent response value, $R_{Cal}$), a particular sensor response value in a detection mode could be associated with a higher level of gas to compensate for the decrease in sensitivity. Other sensors may comprise onboard electronics that provide a digital output. These sensors may be configured to calibrate the sensor's output when exposed to a known concentration of gas and placed in a calibration mode.

If the consistent response, $R_{Cal}$, is below a predetermined threshold, the sensor is considered not to have met the requirements of the calibration. The gas monitor may be configured to provide an audio and/or visual indication that the gas monitor is no longer monitoring that gas.

The results of the tests are transmitted to a remote computer via transceiver 103.

In this way, the gas monitor may be configured to measure trends in the bump test gas curves over time and determine when a sensor is nearing its end of life. In this way, for example, sensor replacement may be scheduled based on the increase in $T_{thresh}$ over a series of bump tests.

Renewal Time Determination

Figure 3A:
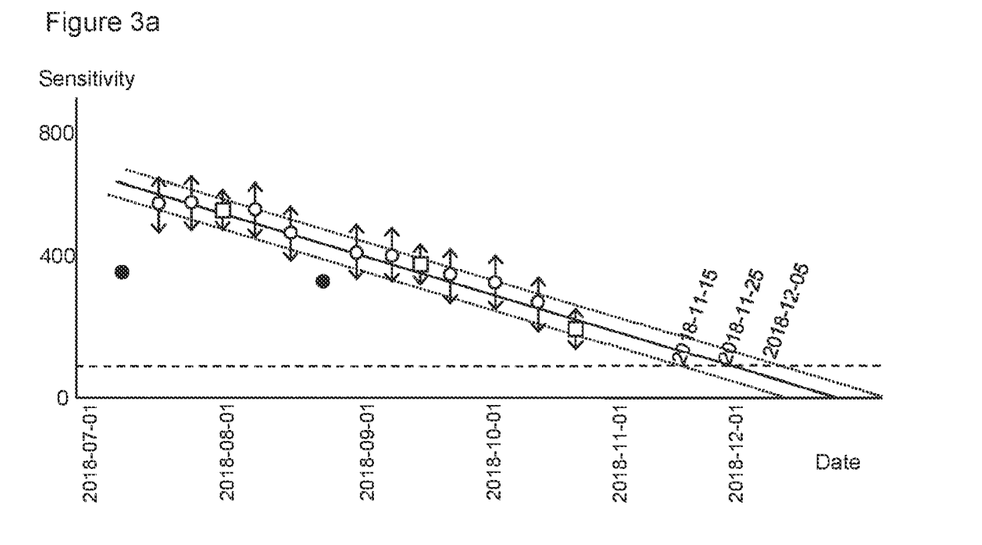
FIG. 3a is a graph of how the sensitivity of the sensor may decay over time.

FIG. 3 shows how the system is configured to calculate the expiry of the sensor based on a number of calibration and bump test sensitivity determinations.

In this case, the gas sensor sensitivity has been repeatedly determined by exposing the gas sensor to a gas and measuring the gas sensor response. This information has been transmitted with information identifying the gas detector, and the time of the calibration to a remote computer. In this case, the transmitted data is associated with a particular gas detector (e.g. using a unique identifier).

The remote computer is then configured to calculate a trend of sensitivity for the gas detector over time based on the received responses and corresponding time values and to determine a renewal time when the calculated trend intersects a predetermined value.

In this case, the sensitivity values are determined by bump tests (shown as hollow circles) as described above (the sensitivity values being determined based on the dynamic response of the gas sensor to the gas) and by calibrations (shown as hollow squares, the sensitivity value being determined based on the stable response of the gas sensor to the gas). In this example, the arrow associated with each determination is a measure of the confidence or error associated with each measurement. The bump-test confidence interval is larger than the calibration confidence interval.

In this case, the method comprises using the remote computer to detect anomalous results by identifying determined sensitivity values which are outside the calculated sensitivity trend.

In this case, detecting anomalous results is done isolating one reading in a series of readings and determining whether that reading is on a consistent trend line with the other readings in the series. In this case, a 5-point rolling window is passed both forward and backward across the time-series data wherein subsequent points in the series are compared to a window aggregate. This results in in data that is dissimilar (defined by coefficients within the outlier algorithm) to the previous or subsequent 5 points being flagged as outliers. It will be appreciated that the number of points in the window may be different (e.g. between 5-10 or more). It will be appreciated that the window may be defined by one or more of: the number of points, the number of calibration points, the number of bump-test points and/or a predetermined time period (e.g. between 10 days and 2 months).

Based on the remaining data (e.g. ignoring the outliers), the remote computer is configured to determine a best fit for the data. In this case, the remote computer is configured to fit the data with a linear decline. In this embodiment, the remote computer is configured to determine the mathematical form of the trend based on sensitivity data received from other gas sensors of the same type. In other embodiments, the remote computer may be configured to determine the mathematical form of the trend based on the data from that sensor itself. In this case the mathematical form is a linear decline.

In this case, the system is configured to determine a range of fits which would be consistent with the determined sensitivity values and their confidence intervals. These various fits allow a range of renewal times to be determined. For example, in this case, the system determines that the likely time that the sensor becomes inoperable will be Nov. 25, 2018±10 days. The system may be configured to report the earliest date (e.g. Nov. 15, 2018 in this case) to ensure that the gas sensor does not become inoperable when needed.

In this case, the renewal time is re-calculated after each new sensitivity value is calculated. It will be appreciated that the accuracy of the expiry date of the gas sensor may become more accurate as the expiry approaches.

Because the bump-test sensitivity values are, in this case, determined by comparing the dynamic response of the sensor during the bump test to the dynamic response of the sensor during calibrations, where the a stable sensitivity value is more accurately determined, as more calibrations are done, the better the remote computer can determine the bump-test sensitivity values, and bump-test confidence intervals.

After a calibration is performed, the remote computer may be configured to adjust a bump-test sensitivity value and/or the confidence interval associated with the sensitivity value based on the calibration.

Figure 4:
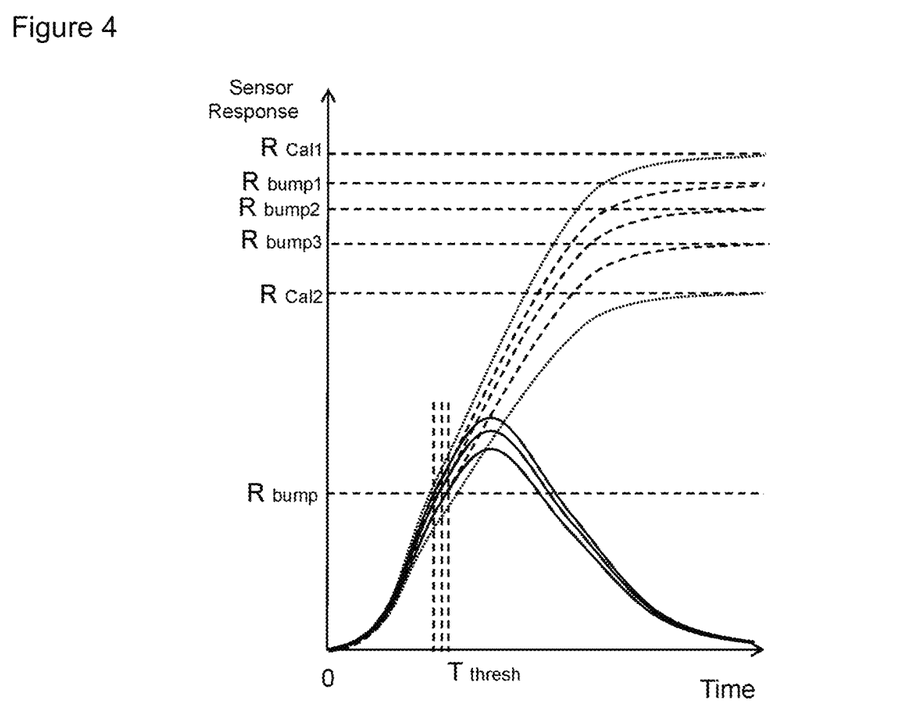
FIG. 4 is a graph of a series of sensor responses across a number of calibrations and bump tests.

FIG. 4 shows how a series of sensitivity value determinations might be made. In this figure:
Recorded calibration responses are shown in dotted lines;
recorded bump test responses are shown as solid lines; and
extrapolated bump test responses (i.e. to correspond to what would happen if a calibration were performed) are shown in dashed lines.

In this case, the first determination is a calibration and the stable response is taken to be the first calibration sensitivity value $R_{Cal1}$. Then a series of three bump tests are performed at intervals. The dynamic response of the sensor during the bump tests are extrapolated (in this case using the form of the response during the calibration) to determine three bump test sensitivity values $R_{bump1}$, $R_{bump2}$, $R_{bump3}$. Then another calibration is performed to provide a second calibration sensitivity value, $R_{Cal2}$. Over this period the sensitivity of the gas sensor has declined.

Typically, a faster rise time would be associated with a lower sensitivity. Therefore, for example, if a bump test with a particular dynamic rise time was associated with a particular bump test sensitivity value, and then a calibration was performed, and the calibration curve had a longer dynamic rise time but a higher stable calibration sensitivity value, the bump test may be adjusted to also have a higher bump test sensitivity value based on the new information provided by the calibration.

Figure 5A:
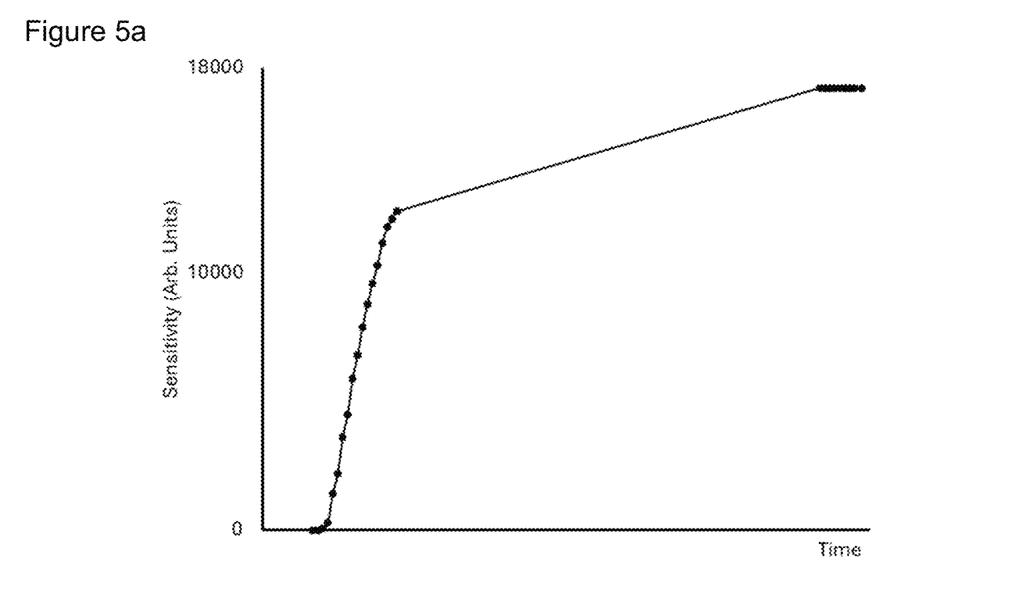
FIG. 5a-c are a series of graphs of sensor responses across a number of calibrations and bump tests.
Figure 5B:
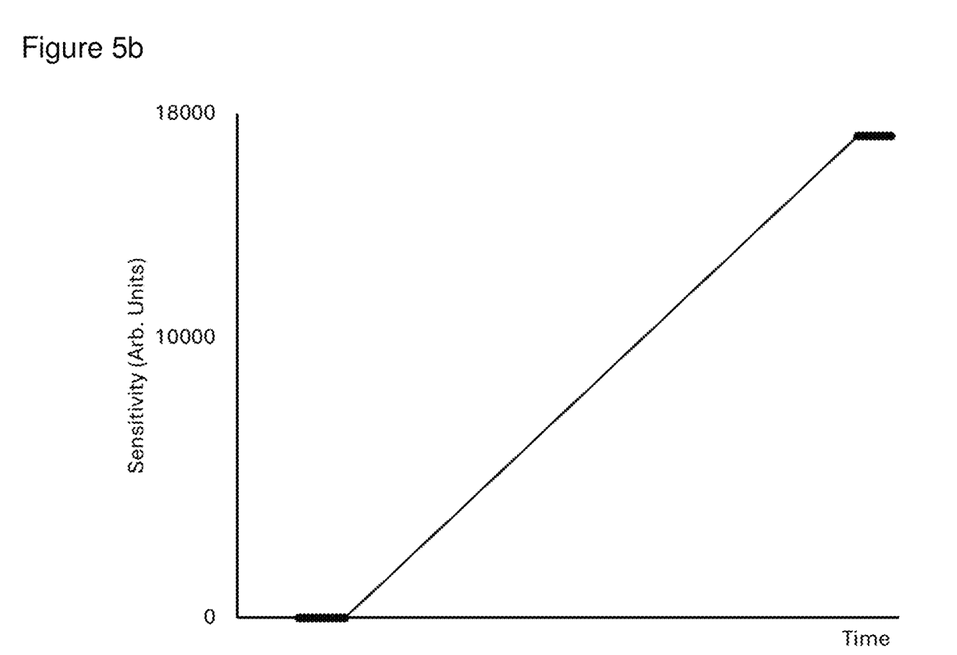
Figure 5C:
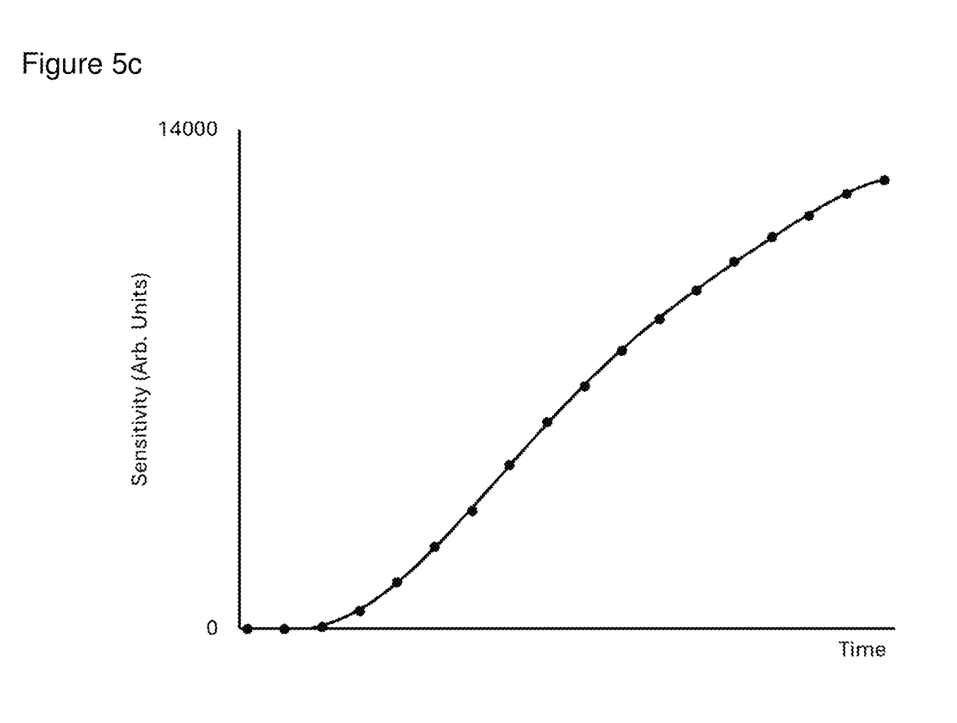

FIGS. 5a-5c show a number of options for determining sensitivity values from calibrations and/or bump tests. In this case, the same cartridge and sensor ($H_2S$) are used for all three tests. It will be appreciated that the readings are connected by straight lines to guide the eye and are not intended to represent interpolated values.

FIG. 5a is example of readings stored for a calibration, the left series being sensor zeroing, and the right series being the span of readings used for calibrating the sensor. If zeroing fails, then the span of readings for calibration are not taken. The time between each pair of readings within each series is 1 second apart. The gap between the last reading in the zeroing set and the first reading in the calibration set is around 90 seconds. By only storing and/or reporting data associated with zeroing and calibration at a time when the sensor response would be expected to be stable reduces the requirements of dealing with excess data.

FIG. 5b is a further example of readings which may be stored for a calibration. In this case, the left series includes the dynamic response of the sensor as it is exposed to the test gas ($H_2S$). As with FIG. 5b, the right series of values being the span of readings used for calibrating the sensor. The gap between the last reading in the zeroing set and the first reading in the calibration set is around 90 seconds.

In the saturation shown in FIG. 5b, the sensor is configured to record and transmit values beyond an inflection point in the graph of the sensor response with respect to time. The inflection point is the point at which the curvature of the graph changes sign and starts to level off towards the calibration value. Including this inflection point may increase the accuracy of sensitivity value compared with just looking at the increasing dynamic response of the sensor (i.e. before the inflection point is reached). Again, omitting to record, transmit and/or store data between the inflection point and the stable response may reduce the amount of data-handling required. However, recording, transmitting and/or storing data associated with the dynamic response of the sensor allows the calibration data to be compared with the responses measured during bump testing as described above.

FIG. 5c corresponds to a set of readings for a bump test, same cartridge and sensor ($H_2S$) as above. All readings are 1 second apart. That is, the bump test in this case takes less than 20 seconds, which is significantly less than performing a full calibration cycle. In this case, the bump test is configured to continue until the inflection point in the graph is reached. This may allow a more accurate determination of the stable sensitivity value.

To obtain the stable sensitivity value, a variety of approaches may be taken. One option is to extrapolate the graph on in time based on the recorded graph and take the value at which the graph reaches a stable value. The shape of the graph may be based on responses recorded for this type of sensor, or the specific sensor being tested (e.g. calibration runs).

For a sensor in a particular concentration of gas under the same conditions, a plurality of non-intersecting graphs of the sensor response are possible depending on the sensitivity of the sensor. Therefore, once the initial dynamic response rise is detected (e.g. during a bump test), it should be possible to determine the particular graph that that dynamic response is associated with. Then, the stable value associated with the particular graph can be identified to give the bump-test sensitivity value. The longer the dynamic response is detected for, the more accurately the particular graph can be identified. As noted above, recording the response to at least the inflection point provides a reasonable accuracy without delaying the user significantly.

Detecting Sensor Replacement

In this case, the remote computer is configured to identify a gas sensor replacement by detecting a jump in sensitivity followed by a decline in sensitivity following a new trend.

Figure 3B:
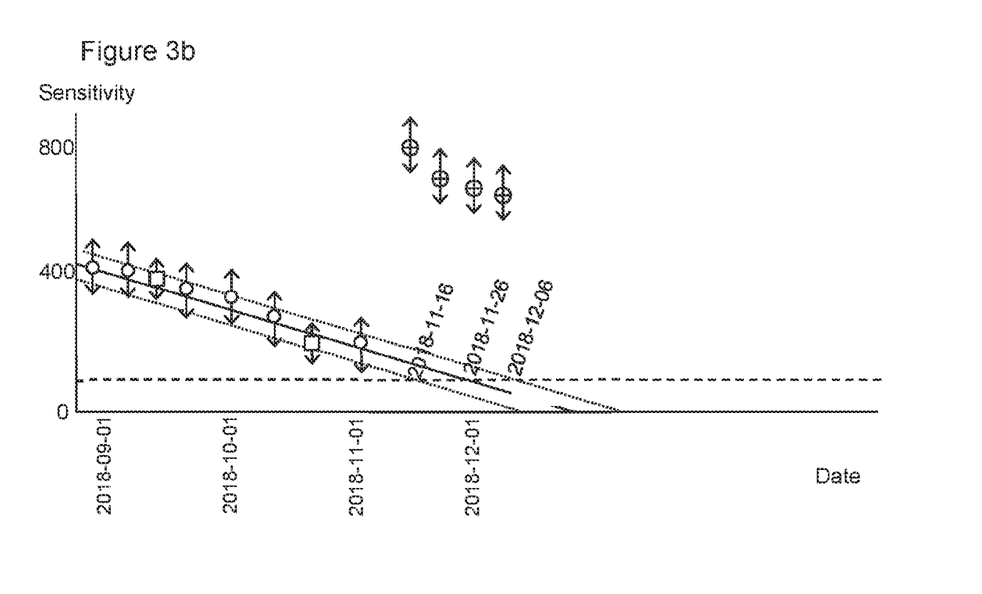
FIG. 3b is a graph of how the sensitivity of a gas detector may change over time as a result of sensitivity decline and sensor replacement.

As shown in FIG. 3b, four anomalous results above the trend line have been identified. Because these are identified as anomalous results, they are not used in calculating the renewal time for the sensor. However, the system is configured to recognize that by themselves, they form a consistent trend, separate to the previous trend line. The system can therefore identify the replacement of a sensor based on detecting a series of sensitivity values which have one or more of the following characteristics:

The series of sensitivity values are above the trend line calculated for the previously determined sensitivity values;

The series of sensitivity values are consistent with each other;

The series of sensitivity values correspond to a marked increase in sensitivity exceeding a predetermined threshold; and The series of sensitivity values correspond to a sudden increase in sensitivity (e.g. taking place within a predetermined period of time or number or sensitivity value determinations).

It will be appreciated that other characteristics may be used.

Situation Monitoring

The response of a gas sensor is typically dependent on its age and prior exposure to a gas, but it may also be dependent on the conditions in which it is placed. For example, the response of a gas sensor may be dependent on the temperature and/or humidity of environment. This means that, if a gas sensor is moved to a new environment or the conditions under which the gas readings are taken change significantly, the trend in sensitivity may no longer be a good indication of when the sensor should be replaced.

In this case, the gas detector is configured to measure environmental conditions at the time of the calibration, and transmit the measured environmental conditions (humidity, pressure and/or temperature) to the remote computer; and wherein the remote computer is configured to calculate the trend of sensitivity based on the most recent determined sensitivities which are within a predetermined environmental condition range.

In addition, the gas detector is configured to measure the location of the gas detector at the time of the calibration, and transmit the measured location to the remote computer; and wherein the remote computer is configured to calculate the trend of sensitivity based on the most recent determined sensitivities which are within a predetermined location range.

Other Options

In some embodiments, the gas monitor may be configured to measure trends in bump test gas curves over time and determine when a calibration is due based on the determined trend. For example, a calibration may be scheduled based on the increase in $T_{thresh}$ over a series of bump tests. Because typically less gas is required for bump tests, predicting when calibration is needed from the bump tests may reduce the overall consumption of test gas. This may allow the gas monitor to remain in the field for longer.

Although the present invention has been described and illustrated with respect to preferred embodiments and preferred uses thereof, it is not to be so limited since modifications and changes can be made therein which are within the full, intended scope of the invention as understood by those skilled in the art.

The invention claimed is:

1. A method for monitoring gas sensor sensitivity, comprising:
   repeatedly determining a gas sensor response from a gas sensor by exposing the gas sensor to a gas; and
   transmitting each gas sensor response, information identifying a gas detector, and calibration time values to a remote computer; and
   using the remote computer to:
      calculate a trend of sensitivity values for the gas detector over time based on the received gas sensor responses and corresponding calibration time values;
      determine a renewal time of the gas sensor when the calculated trend intersects a predetermined value; and report the renewal time.

2. The method according to claim 1, wherein at least one of the sensitivity values is determined by a bump test, wherein the sensitivity values are determined based on a dynamic response of the gas sensor to the gas.

3. The method according to claim 2, wherein the bump test has a duration of less than 45 seconds.

4. The method according to claim 3, wherein the bump test is configured to end before a gas sensor response has stabilized.

5. The method according to claim 4, wherein at least one of the sensitivity values is determined during a calibration, wherein the sensitivity value is determined based on a stable response of the gas sensor to the gas.

6. The method according to claim 5, wherein the gas detector is configured to measure a flow rate of the gas past the gas sensor.

7. The method according to claim 1, wherein the method comprises:
   determining a bump-test sensitivity value by a bump test;
   determining a calibration sensitivity value by a calibration; and
   adjusting, based on the calibration, at least one of: the bump-test sensitivity value and a confidence interval associated with the bump-test sensitivity value.

8. The method according to claim 1, wherein the method comprises:
   determining a bump-test sensitivity value by a bump test;
   determining a calibration sensitivity value by a calibration;
   assigning confidence intervals to the bump-test sensitivity value and the calibration sensitivity value, wherein the bump-test confidence interval is larger than the calibration confidence interval.

9. The method according to claim 8, wherein the method comprises using the remote computer to detect anomalous results by identifying determined sensitivity values which are outside the calculated sensitivity trend.

10. The method according to claim 9, wherein the method comprises using the remote computer to calculate a fit coefficient, the fit coefficient being a measure of a variance of sensitivity data over time with respect to the calculated trend; and to adjust the determined renewal time based on the calculated fit coefficient.

11. The method according to claim 10, wherein the renewal time is re-calculated after each calibration.

12. The method according to claim 11, wherein the gas detector is configured to measure environmental conditions at a time of the calibration, and transmit the measured environmental conditions to the remote computer; and wherein the remote computer is configured to calculate the trend of sensitivity based on most recent determined sensitivities which are within a predetermined environmental condition range.

13. The method of claim 12, wherein the environmental conditions comprise one or more of: humidity, pressure and temperature.

14. The method according to claim 13, further comprising measuring a location of the gas detector at the time of the calibration, and transmit the measured location to the remote computer; and wherein the remote computer is configured to calculate the trend of sensitivity based on the most recent determined sensitivities which are within a predetermined location range.

15. The method according to claim 14, wherein the remote computer is configured to determine a mathematical form of the trend based on sensitivity data received from other gas sensors of a same type.

16. The method according to claim 15, wherein the remote computer is configured to identify a gas sensor replacement by detecting a jump in sensitivity followed by a decline in sensitivity following a new trend.

17. The method according to claim 16, wherein the trend is monitored over at least 3 months and comprises at least 10 received sensitivity values from the gas detector.

18. The method according to claim 17, wherein the gas sensor has a unique identification number which is transmitted with the sensitivity values.

19. A system for monitoring gas sensor sensitivity comprising:
a gas sensor configured to repeatedly determine a gas sensor response by exposing the gas sensor to a gas; and
a remote computer configured to receive each gas sensor response, information identifying a gas detector, and calibration time values;
wherein the remote computer is further configured to:
calculate a trend of sensitivity values for the gas detector over time based on the received gas sensor responses and corresponding calibration time values;
determine a renewal time of the gas sensor when the calculated trend intersects a predetermined value; and
report the renewal time.

20. A method for determining gas sensor sensitivity comprising:
repeatedly performing a bump test by exposing a gas sensor to a gas and measuring dynamic gas sensor responses;
transmitting the dynamic gas sensor responses, information identifying a gas detector, and calibration time values to a remote computer; and
using the remote computer to:
compare the dynamic gas sensor responses to one or more calibration curves;
calculate a trend of sensitivity values for the gas detector over time based on the received dynamic gas sensor responses and corresponding calibration time values; and
determine a sensitivity value of the gas sensor when the calculated trend intersects a predetermined value; and
report the sensitivity value.

* * * * *